United States Patent [19]

Warren

[11] 4,099,519
[45] Jul. 11, 1978

[54] DIAGNOSTIC DEVICE
[76] Inventor: Fred E. Warren, 9205 SW. 91st Ave., #3J, Portland, Oreg. 97223
[21] Appl. No.: 759,353
[22] Filed: Jan. 14, 1977
[51] Int. Cl.² ............................................. A61B 10/00
[52] U.S. Cl. .................................. 128/2.1 R; 128/405
[58] Field of Search ................ 128/2.1 R, 2.1 C, 404, 128/405, 406, 419 R, 419 D

[56] References Cited
U.S. PATENT DOCUMENTS

| 1,789,758 | 1/1931 | Kays | 128/405 |
| 3,128,759 | 4/1964 | Bellis | 128/2.1 R |
| 3,533,397 | 10/1970 | Scher | 128/405 X |
| 3,755,900 | 9/1973 | Friedman | 128/2.1 R X |
| 3,782,366 | 1/1974 | Brown | 128/2.1 R |
| 3,830,226 | 8/1974 | Staub et al. | 128/2.1 R |
| 3,841,311 | 10/1974 | Brown | 128/2.1 R |
| 3,913,588 | 10/1975 | Klomp | 128/419 D |

FOREIGN PATENT DOCUMENTS

| 1,448,644 | 9/1976 | United Kingdom | 128/405 |

Primary Examiner—Robert W. Michell
Assistant Examiner—Lee S. Cohen
Attorney, Agent, or Firm—Kolisch, Hartwell, Dickinson & Stuart

[57] ABSTRACT

Diagnostic and/or therapeutic tool with spaced electrode probe assemblies and piezoelectric element generating electric pulse.

5 Claims, 3 Drawing Figures

DIAGNOSTIC DEVICE

This invention relates generally to diagnostic and therapeutic tools which supply an electric pulse to generate a response in the patient.

Tools of this description have been employed in the past in a number of different ways. For example, the tool may be employed to produce a muscle response or spasm in a patient, through electrically induced neuro-stimulation of the patient.

Conventional apparatus of this description, as proposed in the past, has been subject to a number of disadvantages. For instance, the usual type of equipment has been quite bulky, and many times rather expensive, which limits the use of such equipment to a doctor's office or other locale where such equipment might be expected to be located. Even so-called portable equipment generally has necessitated access to an elecrical source to supply the energy for operating the equipment. Another characteristic of known forms of equipment are voltage and current characteristics tending to produce discomfort in the patient when such is used and also imposing limitations as to the use of the equipment.

A general object of this invention, therefore, is to provide a novel diagnostic and/or therapeutic tool which utilizes an electrical pulse for patient stimulation and which in various forms and embodiments obviates one or more of the above indicated deficiencies.

More specifically, an object of the invention is to provide such a tool which may take the form of a portable instrument, and which includes, as part of such portable instrument, a mechanically operated device which generates the electrical stimulus upon which the tool depends.

A further object and feature of the invention is the provision of a diagnostic and therapeutic tool which employs a piezoelectric element mounted within the device, and means for mechanically stressing such element whereby a relatively high voltage, low current pulse generated therein provides the electrical stimulus upon which the tool operates. The output of the piezoelectric element, when applied to the patient, constitutes a high voltage pulse of extremely short duration and low current magnitude.

The tool in a preferred embodiment of the invention comprises a body, which conveniently may be designed for carrying in one's hand. Extending from such body are a first and a second electrode probe assembly, each terminating in an electrically conductive probe tip, and the probe tips of these probe assemblies being electrically connected to opposite poles of a piezoelectric element which ordinarily is housed in such body. At least one of the electrode probe assemblies includes a flexible reach of conductor cable connecting the described probe tip of the assembly with the body of the tool. The probe tip of the assembly connected by this flexible reach of cable to the body is infinitely adjustable in position at a region remote from the body of the tool. Thus, the two conductive probe tips of the two electrode assemblies may be placed at different relative positions with respect to each other while in contact with different expanses of a patient's body, to vary, as desired, the location and length of the conductive path provided by the patients body between the two probe assemblies. It is additionally comtemplated, in a preferred embodiment of the invention, that the probe assembly which includes the flexible reach of conductor cable be detachably connected to the body of the tool, by a plug and jack connection. When this is done, and when the probe described is disconnected from the tool, with the remaining probe in contact with the patient, and on actuation of the piezoelectric element, an electrical stimulus is applied to the patient of considerably lesser intensity than is the case when the detachable probe assembly is in contact with the patient.

The tool comtemplated by the invention may take various forms and shapes. The specific embodiment of the invention described herein is completely portable, is easily manipulated through the use of two hands and is producible at a cost which is significantly less than the cost of commonly used equipment of today.

These and various other objects and advantages of the invention will become more fully apparent as the following description is read in conjunction with the accompanying drawings wherein.

Figure 1:
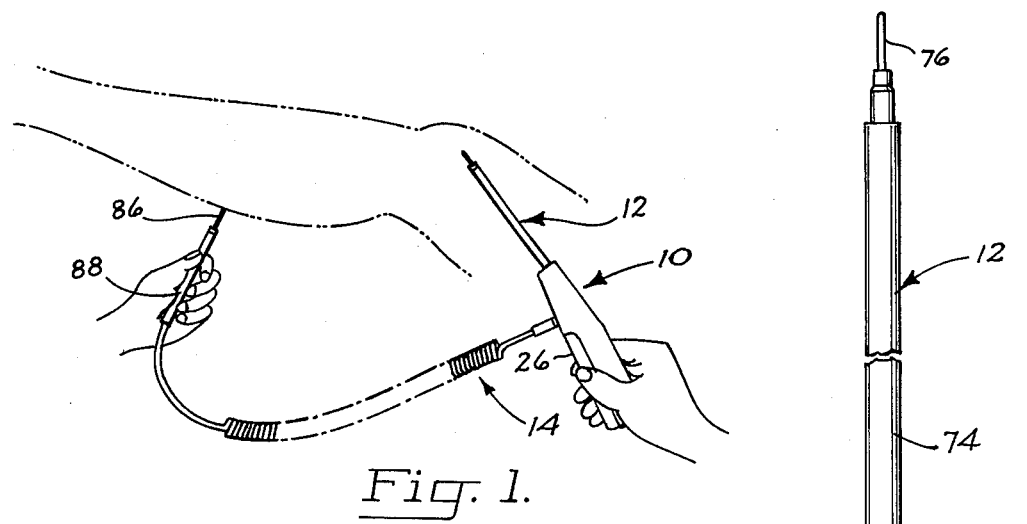
FIG. 1 is a view illustrating use of a tool as comtemplated herein in the production of neuro-stimulation of the knee of a patient.

Referring now to the drawings, the tool illustrated comprises what is referred to herein generally as a body 10, and a pair of electrode probe assemblies 12 and 14, each connected to the body 10 and extending outwardly therefrom.

Figures 2, 3:
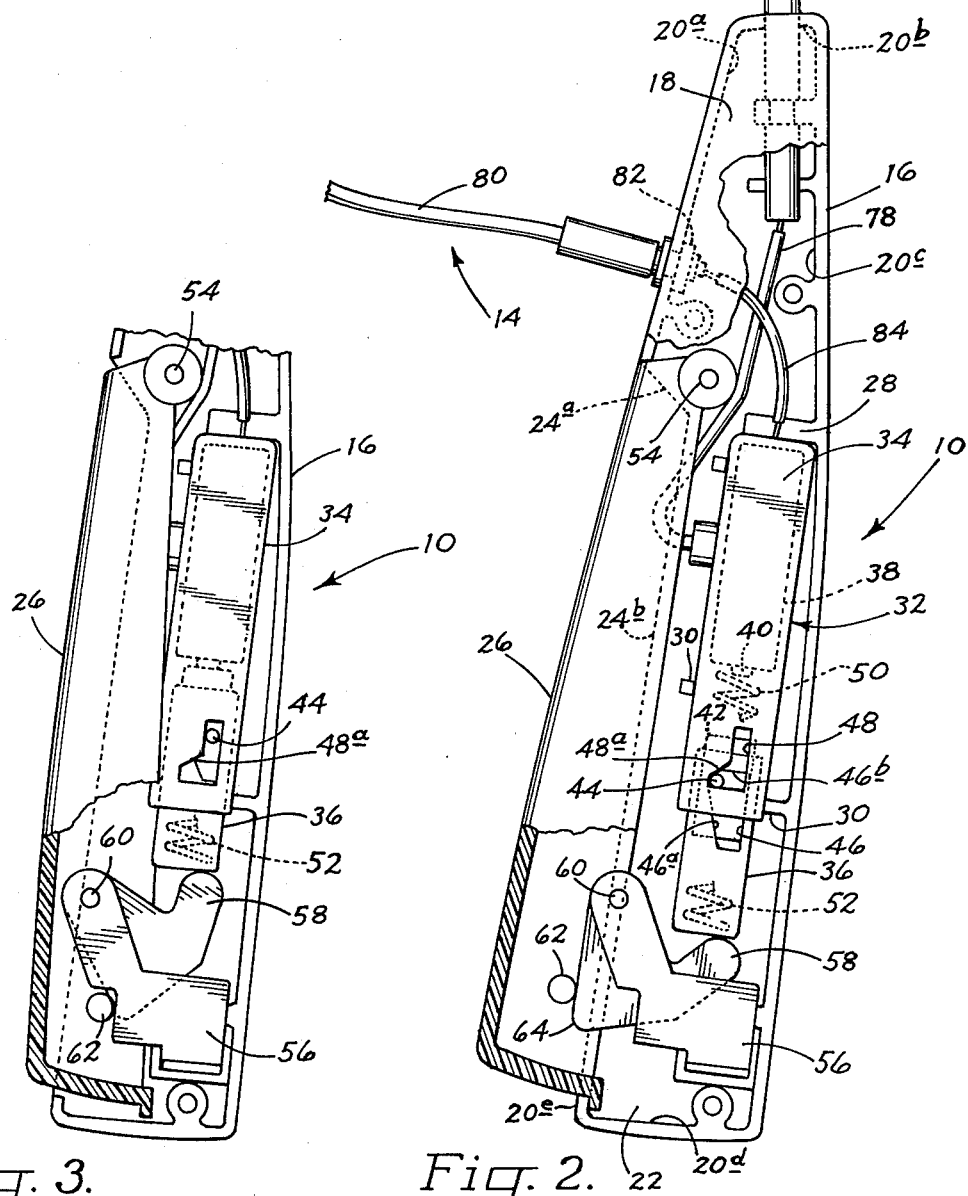
FIG. 2 is a side view of the tool, on a slightly enlarged scale, with portions of said tool broken away.
FIG. 3 is another side view of portions of the tool illustrated in FIG. 2, with parts in the tool occupying a different position of adjustment.

Body 10 is adapted to be held in the hand of the operator, as generally illustrated in FIG. 3 of the drawings.

Body 10 may comprise a pair of substantially allochiral housing sections 16, 18, which may conveniently be made of plastic, suitably secured together in opposed relation. It should be understood that housing section 18 only partially shown in FIG. 2 has substantially the outline of the fully illustrated housing section 16, and has symmetrically the same but opposite configuration, as characterizes allochiral mating parts. With reference to housing section 16, it includes an upstanding, perimetric flange as shown in FIG. 2 extending in reaches 20a, 20b, 20c, 20d, and 20e, which flanges are integral with a wall 22 which closes off the side of the housing which faces away from the viewer in FIG. 2. This flange and the wall impart to the housing section a generally concave configuration as viewed in FIG. 2. With housing sections 16 and 18 joined in opposing relationship, the concavity is shared with an inwardly facing similar concavity in housing section 18, so that the body 10 includes within it a hollow void for the mounting of various parts to be described.

An edge including inclined portion 24a and lineal expanse 24b of wall 22 extends from the bottom end of flange reach 20a in FIG. 2 to the top of flange reach 20e. Housing section 18 includes a similar edge. In this portion of the body therefore, and with the housing sections assembled, an elongate opening is defined which is utilized in the mounting of an elongate trigger element depicted at 26.

Mounted within the space bounded by housing sections 16, 18, and suitably positioned therein as by shoulder 28 and bosses 30 formed as integral parts of the housing sections, is what is referred to herein as a cartridge assembly 32. Such includes an elongate substantially rectangular outer case 34, and projecting out from an open lower end of the case a rectangular inner case 36. Case 36 snuggly fits within the interior of case 34 and is mounted for a reciprocal movement relative to case 34.

Suitably secured within case 34 adjacent its upper end as shown in FIG. 2 is a piezoelectric element 38 terminating at its lower end in a projecting strike portion 40. Mounted within inner case 36 and projecting upwardly slightly from the open upper end of this inner case is an impact hammer 42. The impact hammer is utilized to impart a sharp hammer-like blow against strike portion 40 of the piezoelectric element, whereby the element is mechanically stressed to generate a voltage in the element between opposite poles thereof.

More specifically, hammer 42 is provided with a stud 44 projecting laterally out to one side thereof. Such extends laterally outwardly through an accommodating cutout 46 in case 36 and a cutout 48 in case 34. Cutout 46 includes a cam surface 46a inclined to the longitudinal axis of the cartridge as viewed in FIG. 2, and an edge 46b. Cutout 48 includes a notch 48a.

Interposed between piezoelectric element and inner case 36 is a coiled, partially shown at compression spring 50. Additional spring means partially shown at 52 is interposed between the inner case and impact hammer 42. Spring means 52 exerts an upward bias on the impact hammer relative to the inner case and also tends to turn the hammer to urge stud 44 from right to left as viewed in FIG. 2.

In operation of the cartridge assembly, when inner case 36 is moved upwardly within the outer case from the position shown in FIG. 2, inclined cam surface 46a of cutout 46 bears against stud 44 tending to shift such to the right and out of the notch 48a of cutout 48. With case 36 moved inwardly approximately to the position illustrated in FIG. 3, the stud is released from the notch and spring means 52 then biases the impact hammer upwardly whereby it imparts a striking blow against the piezoelectric element. With release of case 36, spring means 50 (which has greater strength than spring means 52) forces inner case 36 to a fully extended position relative to case 34. As such movement occurs, edge 46b of the inner case engages stud 44 causing retraction of the hammer. On the stud reaching the location of notch 48a in cutout 48, the stud is shifted to seat within the notch by spring means 52, to return the parts to the position shown in FIG. 2.

The mechanism just described is actuated by movement of the trigger element inwardly into the housing. More specifically, the trigger element is pivoted by pivot means 54 to the body of the tool. Mounted within the housing sections is a support 56 pivotly supporting an actuating arm 58 pivoted on the support at 60. A post 62 integral with the trigger element engages shoulder 64 of arm 58. With pivotal movement of the trigger element in a counter-clockwise direction from the position shown in FIG. 2, arm 58 is swung in a counter-clockwise direction about pivot 62 to produce relative inward movement of case 36 within case 34.

Considering the probe assemblies, probe assembly 12 is a rigid probe assembly, in that such includes a rigid sleeve 74 having a lower end in FIG. 2 suitably secured and mounted within the housing sections. The probe includes an electrically conductive probe tip 76 connected by conductor 78 to the positive pole of the piezoelectric element. The rigid probe is generally aligned with the longitudinal axis of the body of the tool, and projects forwardly outwardly therefrom with the tool body held in the palm of the hand as shown in FIG. 1.

Probe assembly 14 constitutes the flexible probe assembly in the unit. Such includes an elongate flexible reach of conductor cable 80. The conductor cable terminates at one end (the end pictured at FIG. 2) in a plug which fits within a jack shown generally at 82 mounted on the housing sections of the body. The conductor within the conductor cable is electrically connected through conductor 84 to the negative pole of the piezoelectric element.

The opposite end of the flexible conductor cable terminates in an electrically conductive probe tip 86 extending outwardly from a sleeve 88. By the inclusion of the flexible reach of conductor cable in the probe assembly, it is possible to position probe tip 86 in an infinite number of positions in a region remote from body 10.

The piezoelectric element employed is preferably one which is made to withstand repeated impacts as results from operation of the tool. Exemplary of piezoelectric elements that are suitable are lead zirconate titanate ceramic elements produced by Gulton Industries, Inc.

Exemplary of a tool which has been successfully used for therapeutic and/or diagnostic reasons is one which produced after impact of the piezoelectric element a voltage of the electrodes which peaked in less than 7 microseconds at a level within the range of 10 to 14 kilovolts and with a current within the low milliamp range, i.e., typically under about 25 milliamps.

It should be obvious from the above description that the tool described has a number of uses. The tool is completely portable, requiring no external energy supply for its actuation. One of the uses of the tool is illustrated in FIG. 1, wherein a neurological response in the knee, is to be determined. The rigid probe may be placed against the kneecap, and the flexible probe assembly may be used to make contact with the body at a place spaced from the knee. When the operator pulls the trigger element inwardly, by squeezing the hand which holds the body of the tool, the mechanism including impact hammer 42 is actuated whereby a sharp blow is imparted to the piezoelectric element generating a sharp electrical pulse applied between the ends of the probe assemblies.

In another form of the tool, the piezoelectric device may be one which is mechanically stressed by pressure generated on squeezing the trigger in the tool. A voltage is generated both on application of pressure, and on relaxation of pressure.

While a particular embodiment of the invention has been described, it should be obvious that modifications and variations are possible as would be apparent to one skilled in the art.

What is claimed and desired to secure by Letters Patent is:

1. A diagnostic and therapeutic tool comprising a portable body assembly adapted for hand manipulation, a first electrode probe assembly mounted on said body assembly terminating in an electrically conductive probe tip disposed outside the body assembly, a second electrode probe assembly mounted on said body assembly terminating in an electrically conductive probe tip disposed outside the body assembly, a piezoelectric element mounted in said body assembly and means electrically connecting the probe tips of the first and second electrode probe assemblies to opposite poles of said piezoelectric element, and trigger actuated means for mechanically stressing the piezoelectric element to generate a voltage in the piezoelectric element which appears directly across said tips.

2. The tool of claim 1, wherein one of said electrode probe assemblies includes an elongated flexible reach of conductor cable flexibly connecting the conductive probe tip of the probe assembly and said body assembly whereby the probe tip is infinitely adjustable in position at a region remote from said body assembly.

3. The tool of claim 2, wherein the flexible reach of conductor cable is connected to said body assembly through a plug and jack connection.

4. The tool of claim 2, wherein said one of said electrode probe assemblies is electrically connected to the negative pole of said piezoelectric element.

5. A diagnostic and therapeutic tool comprising a hand gripped body housing including a finger actuated trigger element movably mounted on said body housing, a piezoelectric element housed within said housing, a jack exposed to one side of said housing electrically connected to the negative pole of said piezoelectric element, a rigid probe assembly extending outwardly from said housing having a conductive probe tip outside of said housing electrically connected to the positive pole of said piezoelectric element, a second probe assembly including a flexible conductor cable terminating at one end in a plug detachably fitting within said jack and terminating at its other end in an electrically conductive probe tip which tip through the cable and said plug and jack connection is electrically connected to the negative pole of the piezoelectric element, and means actuated by said trigger element for mechanically stressing the piezoelectric element to generate a voltage in the piezoelectric element which appears directly across said tips.

* * * * *